United States Patent [19]

Link et al.

[11] Patent Number: 4,641,749

[45] Date of Patent: Feb. 10, 1987

[54] HOLDING STAND FOR SURGICAL INSTRUMENTS

[75] Inventors: Helmut D. Link, Hamburg; Arnold Keller, Kayhude, both of Fed. Rep. of Germany

[73] Assignee: Waldemar Link GmbH & Co., Fed. Rep. of Germany

[21] Appl. No.: 816,588

[22] Filed: Jan. 6, 1986

[30] Foreign Application Priority Data

Jan. 21, 1985 [DE] Fed. Rep. of Germany ....... 3501837

[51] Int. Cl.⁴ ............................................ B65D 85/24
[52] U.S. Cl. .................................... 206/370; 206/372; 206/565; 211/7; 211/60.1; 211/70.8; 248/309.1
[58] Field of Search ...................... 206/370, 372–373, 206/565; 211/7, 60.1, 70.6, 70.8; 248/309.1

[56] References Cited

U.S. PATENT DOCUMENTS

| | | | |
|---|---|---|---|
| 2,452,410 | 10/1948 | Wiegel | 211/60.1 |
| 3,567,034 | 11/1969 | Mozelsio | 211/7 |
| 3,925,014 | 12/1975 | Langdon | 206/370 |
| 4,170,300 | 10/1979 | Pick | 206/572 |
| 4,229,420 | 10/1980 | Smith et al. | 206/370 |
| 4,346,391 | 8/1982 | Schainholz | 206/370 |
| 4,577,755 | 3/1986 | Ramsay | 206/370 |

FOREIGN PATENT DOCUMENTS

| | | |
|---|---|---|
| 2834474 | 2/1980 | Fed. Rep. of Germany . |
| 3004312 | 8/1980 | Fed. Rep. of Germany ..... 211/60.1 |

*Primary Examiner*—William Price
*Assistant Examiner*—Brenda J. Ehrhardt
*Attorney, Agent, or Firm*—Townsend and Townsend

[57] ABSTRACT

Holding stand for surgical instruments which has a comb bar having receiving recesses for instrument shafts. To secure or release simultaneously all of the instrument shafts in the associated receiving recesses, a locking bar is allocated to the comb bar, which locking bar is arranged adjacent and parallel to the comb bar and can be moved relative to the comb bar in the longitudinal direction and, at each receiving recess of the comb bar, has a locking lug which, as a result of the displacement, can be pushed over the instrument shaft or removed from the latter, which instrument shaft is located in the receiving recess.

11 Claims, 5 Drawing Figures

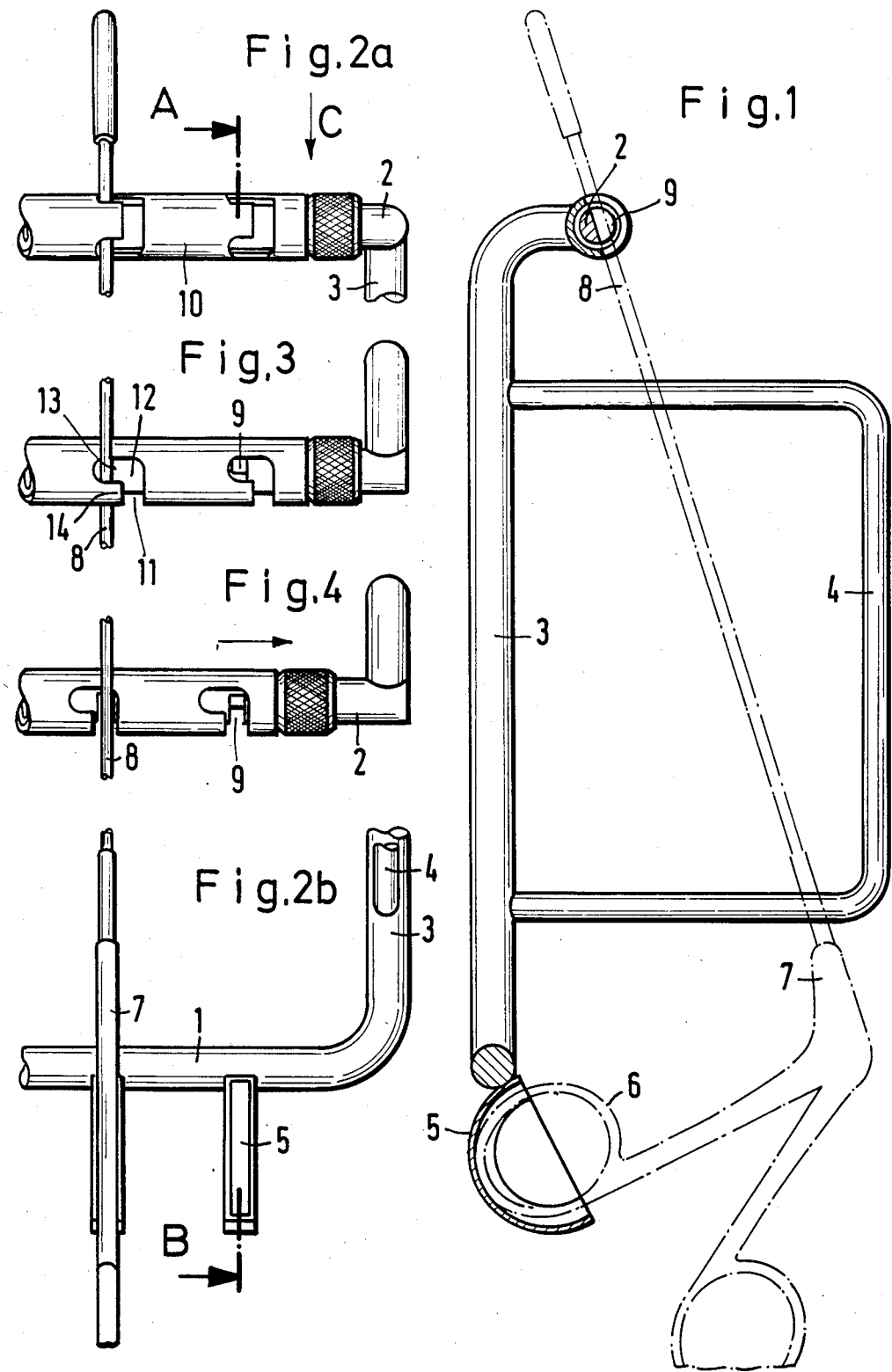

4,641,749

HOLDING STAND FOR SURGICAL INSTRUMENTS

DESCRIPTION

The invention relates to a holding stand for surgical instruments which has a comb bar having receiving recesses for instrument shafts.

For supporting surgical instruments, storage and sterilising stands are used which have adequately reliable receiving devices for transport and storage. For example, these receiving devices for receiving longitudinally extended instrument parts, which in the present context are simply designated without restrictive intent as shafts, can be made as a series of recesses in a bar which, because of its design, can be designated as a comb bar. These receiving recesses can be supplemented for each instrument by further holding devices which are made exactly the same or different without this being of importance for the invention. For utilisation, the instruments must be able to be removed easily from the receiving recesses. Therefore they must not be made for transport reliability such that their removal could be impaired. The object of the invention is to create a holding stand of the type mentioned at the beginning, from the receiving recesses of which the instruments can be easily removed and which nevertheless ensures complete holding reliability if required.

The solution according to the invention is that, adjacent and parallel to the comb bar, a locking bar is mounted which, at the receiving recesses of the comb bar, has in each case a receiving opening and a locking lug which projects in the longitudinal direction into the receiving opening and, by longitudinal displacement of the locking bar relative to the comb baer, can be moved into a locking position, in which the locking lug grips over the instrument shaft lying in the receiving recess and the receiving opening, and into a release position, in which the locking lug lies next to the receiving recess.

The invention leads to a design which, on the one hand, enables a receiving recess configuration facilitating removal and, on the other hand, permits absolute transport safety, with the design nevertheless being simple, which is of importance with regard to freedom from trouble and ease of operation and maintenance.

In general, the comb bar will be of a fixed arrangement and the locking bar of a movable arrangement, since the receiving recesses in the comb bar are to determine the position of the instruments and not alter the position by the locking actuation. However, a reversed arrangement is not to be excluded for the exceptional case.

A particularly simple arrangement is obtained when one of the two bars is hollow and the other is arranged and guided in the said hollow bar; namely, expediently in the form that the comb bar is of a fixed arrangement and the locking bar is made as a tube which can be displaced on the comb bar.

The invention is described in greater detail below with reference to the drawing which depicts an advantageous illustrative embodiment and wherein:

FIG. 1 shows a sectional side view,

FIGS. 2a and 2b show two partial plan views which complement one another with regard to FIG. 1 which represents the section A-B, and FIGS. 3 and 4 show partial end views in the direction of view C of FIG. 2a.

The stand has a closed tubular frame which is formed from two bars 1 and 2, which are parallel to one another, and two bars 3 connecting the bars 1 and 2 at right angles. Since only one end of the stand appears in FIGS. 2 to 4, only one end section each of the bars 1 and 2 and of the bars 3 can be seen. The bars 1 and 3 lie in one plane and form the seating surface for the stand, by means of which it can be placed onto a support surface, whereas the bar 2 is raised from the plane of the bars 1 and 3 by tube bending. An arched handle 4 is attached to each of the bars 3 in a plane vertical to the seating surface.

A plurality of holding devices 5 is fixed to the bar 1 which, in the example shown, are designed as bearing shells, turned out semicircularly, for receiving a ring 6 of a ring grip instrument 7 which has an extended shaft 8. Opposite each bearing shell 5, a receiving recess 9 for receiving a shaft 8 is provided in the bar 2. With respect to the receiving recesses, the bar 2 is designated as a comb bar. The recesses 9 are simply milled into the comb bar 2 at right angles to the longitudinal direction of the latter and have a width and depth adapted to the particular shaft to be located.

The comb bar 2 is enclosed by a tube 10 which, at the receiving recesses 9 of the comb bar, contains angular receiving openings 11 which comprise a part 12, running essentially at right angles to the tube longitudinal direction, and a part 13 running in the longitudinal direction, with the latter being covered by a lug 14 running in the longitudinal direction. The part 12 is at least as wide as the associated receiving recess 9. The section 13 is generally to be of a length which is also equal to this width; but this is not absolutely necessary.

The tube 10 can be displaced as a locking bar in the longitudinal direction on the comb bar 2. Its first end position, shown in FIG. 4, is the release position, in which the part 12 of the receiving opening 11 lies over the receiving recess 9 and therefore enables an instrument shaft 8 to be inserted into the receiving recess 9 or removed from the latter. If the tube 10 forming the locking bar is displaced in the direction of the arrow (FIG. 4), it moves into the locking position shown in FIGS. 2a and 3 in which the lug 14 grips over the receiving recess 9 and therefore prevents removal of the shaft 8.

It is essential that all of the receiving recesses provided in the comb bar 2 can be locked or opened by one and the same movement of the locking bar. Utilization of the device is therefore extremely simple.

It can be recognised that the principle is independent of the particular configuration of the surgical instruments to be received, because the position and shape of the receiving recesses and receiving openings can be adapted within wide limits to the particular instrument part to be received.

In the illustrative embodiment, the locking lug 14, in the locked position, lies directly above the associated receiving recess of the comb bar. However, the arrangement can also be made such that the locking lug is pushed at another, adjacent location above the instrument shaft lying in the receiving recess. The comb bar and the locking bar can therefore also be arranged next to one another instead of above one another or around one another.

We claim:

1. A medical instrument holder comprising:
a base having first and second ends;

a first end bar, mounted at the first end of the base, including a plurality of instrument handle receptacles;

a second end bar, mounted at the second end of the base, comprising a notched comb bar and a locking bar, the comb and locking bars mounted to one another for relative movement between locking and open positions, the comb bar having first notches sized to receive the shafts of the medical instruments, the locking bar having second notches, the first and second notches having respective first and second open ends aligned when the locking and comb bars are in the open position, the first and second open ends being offset when the locking and comb bars are in the locking position to retain the shafts in the first notches; and a handle, including a gripping surface, attached to the base, the gripping surface spaced apart from the base at a chosen position so the gripping surface may be easily grasped without contacting a medical instrument supported by one of the instrument handle receptacles and the second end bar.

2. The medical instrument holder of claim 1 wherein the instrument handle receptacles are upwardly opening receptacles.

3. A medical instrument holder as recited in claim 1, wherein one of the comb and locking bars includes a tubular outer bar having a longitudinal hollow opening and the other of the comb and locking bars includes an inner bar sized to fit within the longitudinal hollow opening.

4. The medical instrument holder of claim 3 wherein the outer bar is the locking bar and the inner bar is the comb bar.

5. The medical instrument holder of claim 3 wherein the outer bar is cylindrical in shape.

6. The medical instrument holder of claim 3 wherein the inner bar is solid.

7. The medical instrument holder of claim 3 wherein the inner bar is cylindrical in shape.

8. The medical instrument holder of claim 1 wherein the base extends in a generally horizontal plane and the second end bar is positioned parallel to and vertically above the plane.

9. The medical instrument holder of claim 8 wherein the gripping surface is positioned perpendicular to and above the second end bar.

10. The medical instrument holder of claim 1 wherein the instrument handle receptacles include an arcuate bottom surface and side walls.

11. A medical instrument holder comprising:

a base extending generally horizontally and having first and second ends;

a first end bar, mounted at the first end of the base, including a plurality of instrument handle receptacles;

a second end bar, mounted at the second end of the base positioned parallel to and vertically above the plane of the base, comprising an inner bar of cylindrical shape having first notches sized to receive the shafts of the medical instruments, and an outer tube sized to slide in a longitudinal direction over the inner bar and having second notches, the first and second notches having respective first and second open ends aligned when the inner bar and outer tube are in the open position, the first and second open ends being offset to retain the shafts in the first notches when the inner bar and outer tube are in the locking position; and a handle, including a gripping surface attached to the base positioned so the gripping surface may be easily grasped without contacting the medical instrument supported by one of the instrument handle receptacles and the second end bar.

* * * * *